United States Patent [19]

Okada et al.

[11] Patent Number: 5,167,637
[45] Date of Patent: Dec. 1, 1992

[54] VALVE MEMBRANE FOR A CATHETER INTRODUCER HEMOSTATIC VALVE

[75] Inventors: Yosuke Okada; Hideyuki Makino, both of Shizuoka, Japan

[73] Assignee: Sherwood Medical Company, St. Louis, Mo.

[21] Appl. No.: 785,575

[22] Filed: Oct. 30, 1991

[30] Foreign Application Priority Data

Nov. 1, 1990 [JP] Japan .................. 2-293521

[51] Int. Cl.⁵ .............................................. A61M 5/00
[52] U.S. Cl. .................. 604/167; 251/149.1; 604/256
[58] Field of Search ............... 604/158, 164, 167, 169, 604/256; 251/149.1; 137/843, 844

[56] References Cited

U.S. PATENT DOCUMENTS

| Re. 21,699 | 1/1941 | Monnier | 215/37 |
|---|---|---|---|
| 2,023,267 | 12/1935 | de Saint Rapt et al. | 128/141 |
| 2,436,291 | 2/1948 | Daniel | 215/43 |
| 3,659,587 | 5/1972 | Baldwin | 128/2 F |
| 4,244,379 | 1/1981 | Smith | 128/766 |
| 4,430,081 | 2/1984 | Timmermans | 604/256 |
| 4,610,665 | 9/1986 | Matsumoto et al. | 604/167 |
| 4,626,245 | 12/1986 | Weinstein | 604/167 |
| 4,673,393 | 6/1987 | Suzuki et al. | 604/167 |
| 4,798,594 | 1/1989 | Hillstead | 604/167 |
| 4,895,346 | 1/1990 | Steigerwald | 251/149.1 |
| 4,895,565 | 1/1990 | Hillstead | 604/167 |
| 4,929,235 | 5/1990 | Merry et al. | 604/167 |
| 4,932,633 | 6/1990 | Johnson et al. | 604/256 |
| 4,944,736 | 7/1990 | Holtz | 604/403 |
| 4,946,133 | 8/1990 | Johnson et al. | 251/149.1 |
| 5,000,745 | 3/1991 | Guest et al. | 604/256 |
| 5,006,113 | 4/1991 | Fischer | 604/167 |

FOREIGN PATENT DOCUMENTS

| 344907 | 12/1989 | European Pat. Off. | 604/167 |
|---|---|---|---|
| 91/10459 | 7/1991 | World Int. Prop. O. | 604/167 |

*Primary Examiner*—Paul J. Hirsch
*Attorney, Agent, or Firm*—Andrew J. Beck; Montgomery W. Smith; Curtis D. Kinghorn

[57] ABSTRACT

A hemostasis valve membrane for use with a catheter introducer having a cover and a frame is disclosed. The valve membrane is inserted between the cover and the frame of the catheter introducer body. The valve membrane is a disc made of a soft elastic material. The disc has opposed faces, at least one of which has a concave shape extending into the disc. A plurality of slits extend into the disc from the faces so that slits extending into the disc from one face do not touch slits extending into the disc from the opposed face. A needle hole connects the slits extending into the disc from one face with the slits extending into the disc from the opposed face.

17 Claims, 3 Drawing Sheets

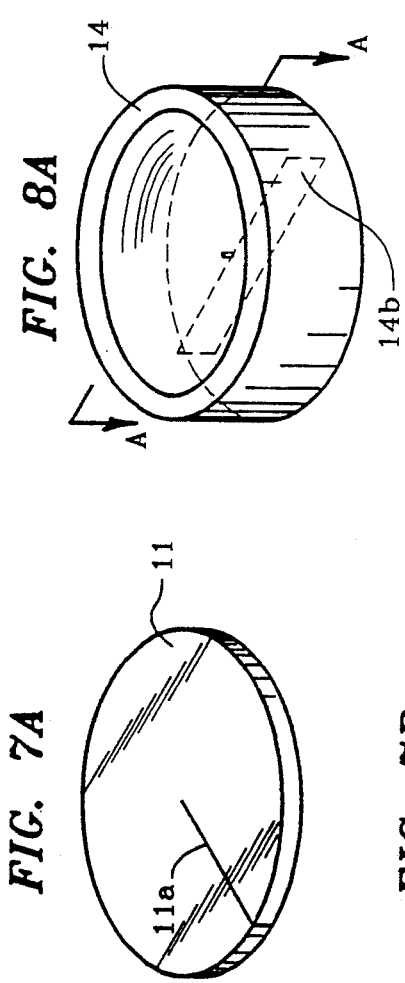
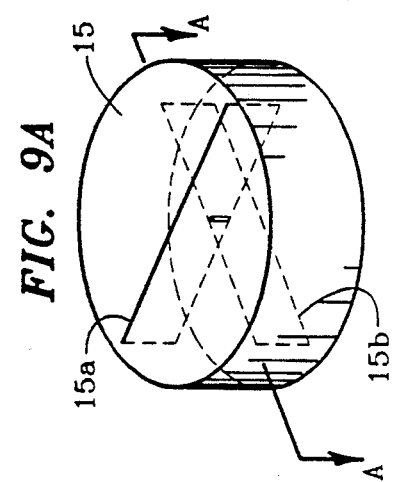
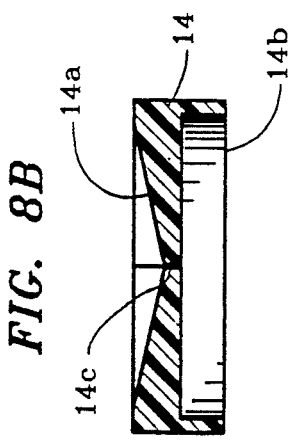
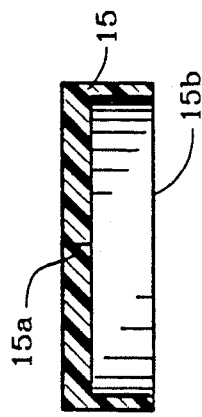
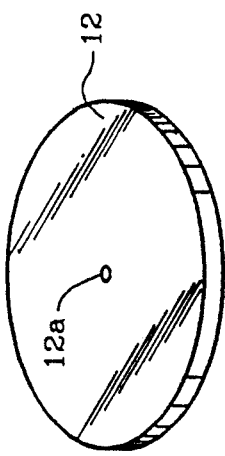
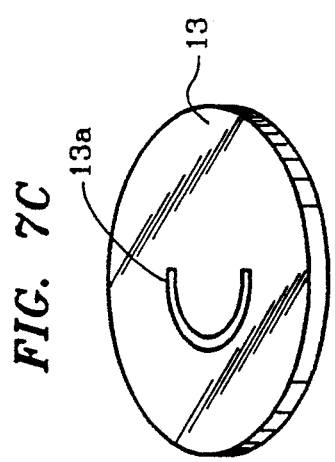

VALVE MEMBRANE FOR A CATHETER INTRODUCER HEMOSTATIC VALVE

BACKGROUND OF THE INVENTION

1. Field of the Invention

The present invention concerns a catheter introducer hemostatic valve which is utilized for diagnoses and treatments by means of blood vein imaging.

2. Description of the Related Art

A catheter introducer has heretofore been utilized as a tool for inserting a blood vein imaging catheter into a blood vein. FIG. 5 shows a profile view of said catheter introducer. In the FIGURE, (1) is a blood vein, (2) is an incision, (3) is a catheter introducer, (5) is its sheath, (6) is its director, (7) is a guide wire, and, (8) is a catheter.

During surgery, the skin in the vicinity of the objective blood vein (1) is cut, and as a result, the incision (2) is formed. After a hollow needle (not indicated in the FIGURE), into which an inner needle (not indicated in the FIGURE) has been inserted, has been introduced into the blood vein (1) via the incision (2), the inner needle is removed. After the guide wire (7) has been inserted into the hollow needle, the hollow needle is removed in such a way that only the guide wire will remain. Subsequently, the catheter introducer (8), into which the director (6) has been inserted, is inserted into the blood vein (1) by using the guide wire (7) as a guide. After the sheath (5) of the catheter introducer has been inserted into the blood vein (1), the director (6) and the guide wire (7) are removed. After the catheter (8) has subsequently been inserted into the sheath (5), the front end of the catheter is guided into the blood vein (1), and as a result, the insertion of the catheter (8) into the blood vein (1) is completed.

During the aforementioned process whereby the catheter (8) is inserted into the blood vein (1), the following problem is observed. For example, if the catheter introducer (3) is inserted into the blood vein (1), if the director (6) and guide wire (7) are removed while the sheath (5) remains in the blood vein (1), and if the catheter (8) is inserted into the catheter introducer (3) and then guided to the blood vein (1), the blood in the blood vein (1) may leak from the catheter introducer (3) as a result of a back flow. To prevent this, a hemostatic valve is attached to the catheter introducer mainframe (4).

FIG. 6 shows an example of conventional hemostatic valves. In FIG. 6, (a) shows a cross-sectional view of the mainframe, whereas (b) shows an oblique view of the hemostatic valve. The hemostatic valve is obtained by inserting a laminate consisting of the valve membrane (9), which possesses the small hole (9a) at the center, and the valve membrane (10), which possesses the Y-shaped slit (10a) at the center, into a gap between the lid (4a) and cylindrical frame (4b) of the mainframe (4). Both the valve membranes (9) and (10) are composed of an elastic material, and since the small hole (9a) and the slit (10a) are present at the center, the valve membranes (9) and (10) are elastically gravitated toward the outer circumferences of the guide wire (7) and catheter (8) when the guide wire (7) and catheter (8) are transmitted through the valve membranes (9) and (10). As a result, the leakage of blood within the mainframe (4) can be prevented, and when the guide wire (7) and catheter (8) are removed, the slit (10a) of the valve membrane (10) is contiguously attached, and as in the aforementioned case, the leakage of blood in the mainframe (4) can be prevented. The hemostatic valve of a catheter introducer serves the aforementioned functions.

In addition to the embodiment of a valve membrane for a catheter introducer hemostatic valve obtained by laminating multiple valve membranes shown in FIG. 6, it is also possible to laminate three valve membranes (11), (12), and (13), which possess the slit (11a), small hole (12a), and the U-shaped channel (13a), respectively (see FIG. 7).

Instead of laminating multiple valve membranes for constituting a catheter introducer hemostatic valve, as in the aforementioned case, there have been many cases in recent years where the functions of multiple valve membranes are assumed by a single valve membrane. Such an example is shown in FIGS. 8 and 9. In the FIGURE, (a) shows an oblique view, and (b) shows a cross-sectional view of the A—A segment. In the valve membrane (14) shown in FIG. 8, the basin-shaped depression (14a) is formed on one surface, whereas the slit (1b) is formed on the other surface, and the center of the depression (14a) and the center of the slit (14b) are linked via the small hole (14c). In the valve membrane (15) shown in FIG. 9, linear slits (15a) and (15b), which perpendicularly intersect one another, are formed on both surfaces. Thus, various structures have been proposed for catheter introducer hemostatic valves.

As has been mentioned above, various types of catheter introducer hemostatic valves have been proposed. The following are necessary conditions for hemostatic valves: (1) there may be no leakage of blood, etc. even when a small-diameter guide wire is transmitted; (2) a large-diameter director or catheter must be smoothly inserted and retracted without resistance; (3) there may be no leakage even in a state where nothing has been inserted.

The aforementioned hemostatic valves obtained by laminating multiple valve membranes somewhat satisfy the aforementioned conditions. When a large-diameter cylinder is repeatedly inserted and retracted, however, the valve begins to fail to fit tightly, and when the cylinder is removed, leakage may be observed. If the thickness of the valve membrane is enlarged in order to prevent said leakage, the leakage can be reduced, but since the inserting resistance increases, the operation becomes difficult.

In the integrated valves shown in FIGS. 8 and 9, some improvements are made as compared with the laminated valves. When a guide wire is quickly inserted and retracted, however, leakage tends to occur, and it is difficult to sufficiently lower the insertion resistance of a large-diameter cylinder. In particular, when a small-diameter guide wire is inserted into the valve membrane shown in FIG. 9, the presence of the slit intersection in the middle, which tightens the guide wire, is more advantageous as compared with a valve which possesses a slit which is open to both surfaces. Even in this case, however the gap (16) is produced, as FIG. 9 (c) indicates, and leakage is inevitable.

SUMMARY OF THE INVENTION

The present invention, which has been proposed in response to the aforementioned problems inherent in conventional devices, is a valve membrane for a catheter introducer hemostatic valve which is capable of preventing blood leakage completely and which remains lubricated when a catheter, etc. are inserted or retracted.

In order to achieve the aforementioned objective, the present invention provides a valve membrane for a catheter introducer hemostatic valve obtained by inserting a valve membrane into a gap between the lid and cylindrical frame of a catheter introducer mainframe. The valve membrane is characterized by a disc shape consisting of a soft and elastic material; a first slit is formed on the surface which passes the central axis of the valve membrane and, which is open to only one surface of the valve membrane; a second slit is formed on the opposite surface which is characterized by a depth that will not be contacted with the first slit, which passes the central axis of the valve membrane, and which is open to the opposite surface; and, a small hole formed at the middle of the valve membrane, the diameter of which is slightly smaller than the diameter of a guide wire and which links the centers of said two slits.

With the invention, the following excellent effects are attained: (1) The leakage of blood, which is produced as a result of a back flow into the mainframe of a catheter introducer, can be prevented during the insertion and retraction of a guide wire or catheter; and, (2) the guide wire or catheter can be smoothly inserted or retracted.

If a small-diameter guide wire is transmitted through the center of the aforementioned hemostatic valve, the guide wire is inserted into the slit and small hole which have been formed on the hemostatic valve membrane. The diameter of the small hole is slightly smaller than the diameter of the guide wire. If the diameter and length of the small hole are properly selected and if an appropriate valve material is selected, not only small-diameter guide wires but also large-diameter catheters can be inserted into the hemostatic valve.

The soft and elastic material constituting the valve presses the outer circumference of a cylinder (e.g., guide wire, etc.) inserted into the small hole, and as a result, the leakage of blood, etc. can be prevented. Since valve slit-forming segments are present on both sides of the small hole, the hemostatic valve exhibits a sufficiently high pressure resistance even if the length of the small hole is somewhat reduced and if the hardness of the valve membrane material is lowered.

BRIEF DESCRIPTION OF THE FIGURES

FIG. 5 (b) shows a profile view of the catheter introducer in a case where a catheter is inserted.

FIGS. 7, 8 and 9 show oblique or cross-sectional views of a conventional valve membrane.

DETAILED DESCRIPTION OF THE INVENTION

In the FIGURES, the reference numbers denote the following: (1): blood vein; (3): catheter introducer; (7): guide wire; (8): catheter; (20), (21), (22), and (23): valve membranes; (20a), (20b), (21a), (21b), (22a), (22b), (23a), and (23b): slits; (20c), (21c), (22c), and (32c): small holes; (24) basin-shaped depression.

In the FIGURES, identical notations signify identical or equivalent components.

Figure 1A:
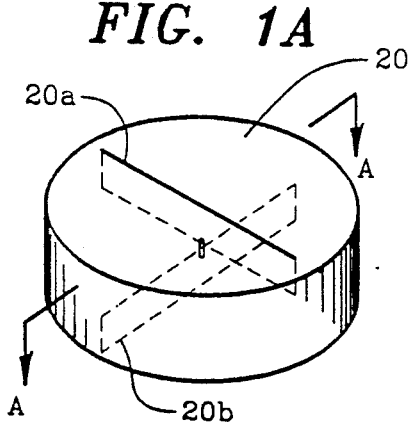
FIG. 1 pertains to a valve membrane for a catheter introducer in one embodiment of the present invention where (a) shows an oblique view and (b) shows a cross-sectional view of the A—A segment.
Figure 1B:
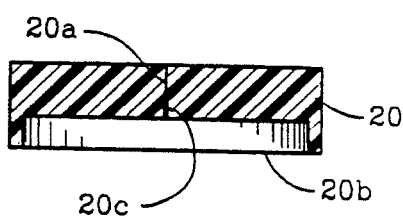

As the FIGURES indicate, the valve membrane (20) for the catheter introducer hemostatic valve is shaped in the form of a disc by using a soft and elastic material. In the embodiment of FIG. 1, a pair of linear slits (20a) and (20b) are formed on both surfaces of the disc. Slits (20a) and (20b) are opened to their respective surface alone, which pass the central axis of the valve membrane, and which are characterized by depths which prevent mutual contacts. A small hole or needle hole (20c) which links the centers of the slits (20a) and (20b) is located in the middle of the valve membrane (20).

Synthetic rubbers, etc. can be utilized as the soft and elastic material constituting the valve membrane (20). The diameter of the small hole (20c) is slightly smaller than the diameter of the guide wire (7). Its length is optimized in consideration of the catheter introducer specifications.

The aforementioned valve membrane (20) is inserted into a gap between the lid (4a) and cylindrical frame (4b) of the catheter introducer mainframe (4), and as a result, a hemostatic valve is formed. If the guide wire (7) is inserted into the middle of the hemostatic valve, the guide wire (7) is transmitted through the slit (20a), small hole (20c), and slit (20b) of the valve membrane (20). In such a case, the wire (7) is transmitted through the small hole (20c), which is characterized by a diameter smaller than the wire diameter. As a result, the small hole (20c) is elastically deformed, and the outer circumference of the wire (7) is pressed by the valve membrane. Since the slits of the valve membrane (20) press the small hole (20c) from both sides, the leakage of blood in the mainframe (4) can be prevented. If the diameter and length of the small hole and the material and hardness of the valve membrane (20) are, properly selected, the catheter (8), which is characterized by a diameter larger than that of the guide wire (7), can also be inserted. At the same time, the blood leakage can be prevented.

Figure 2A:
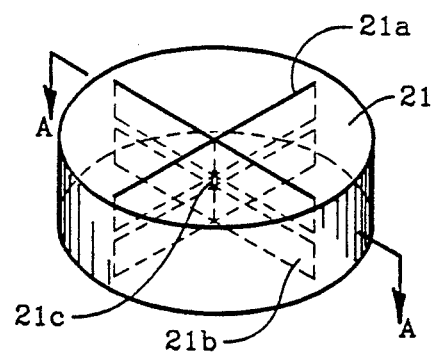
FIGS. 2, 3 and 4 pertain to other embodiments of the invention where in each FIG. (a) shows an oblique view and (b) shows a cross-sectional view of the A—A segment.
Figure 2B:
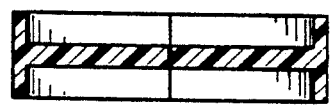
Figure 3A:
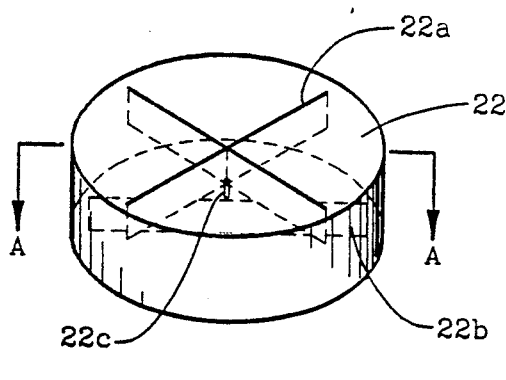
Figure 3B:
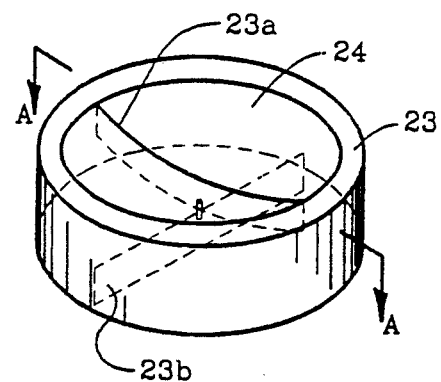
Figure 4A:
Figure 4B:
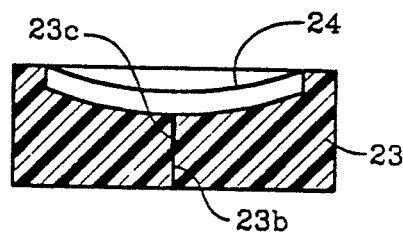
Figure 5A:
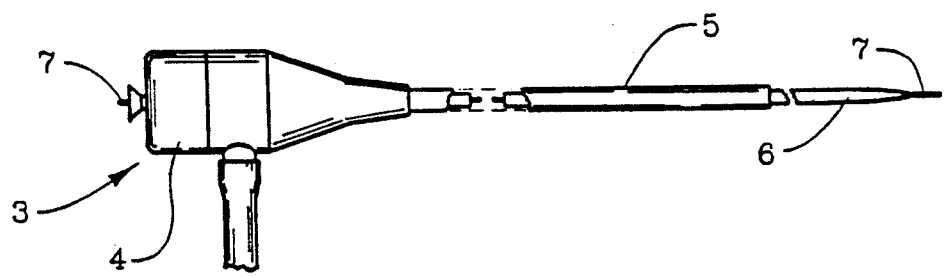
FIG. 5 (a) shows a profile view of a catheter introducer in a case where a director equipped with a guide wire is inserted.
Figure 5B:
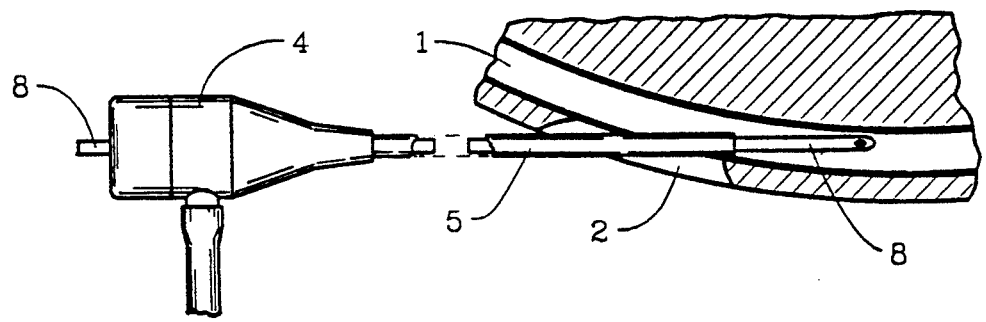
Figure 6A:
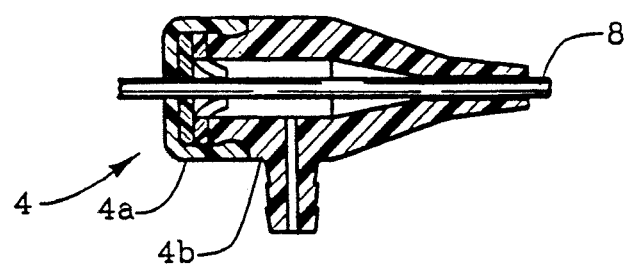
FIG. 6 pertains to a conventional catheter introducer where (a) shows a cross-sectional view of the mainframe and (b) shows an oblique view of the hemostatic valve.
Figure 6B:
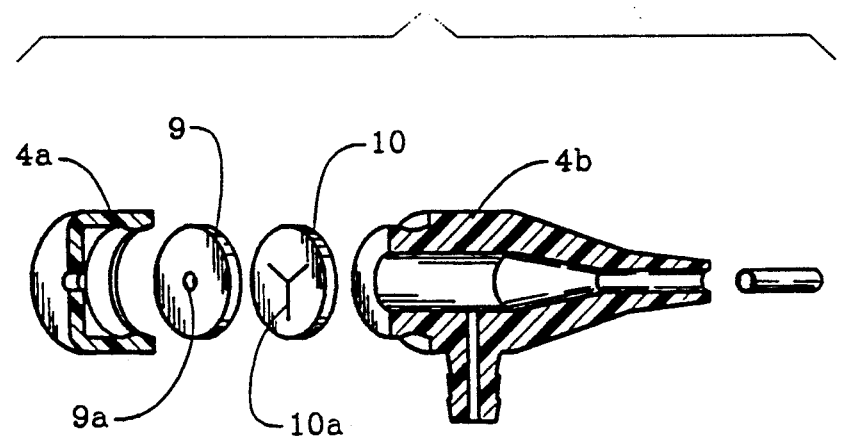

The slit and small hole configurations on the valve membrane (20) are in no way restricted to those shown in the embodiment of FIG. 1, and other structures can be utilized. FIGS. 2 through 4 pertain to other embodiments of the valve membrane where (a) shows an oblique view and (b) shows a cross-sectional view of the A—A segment. The valve membrane (21) of FIG. 2 is characterized by a structure wherein slits (21a) and (21b), which are formed on each surface, are configured in the form of a "cross" which intersects the center of the plane, and two slits are configured in opposition to one another.

In FIG. 3, the aforementioned two cross-shaped slits are configured without opposition.

FIG. 4 pertains to an embodiment where a basin-shaped or concave depression (24) is formed on one surface of the valve membrane (23). Linear slit (23a) is formed on the basin-shaped or concave surface and slit (23b) is formed on the surface opposite the basin-shaped or concave surface. Small hole (23c) is formed which links the centers of the slits (23a) and (23b).

We claim:

1. A hemostasis valve membrane for use with a catheter introducer having a cover and a frame, said valve membrane for inserting between the cover and frame of the catheter introducer body, said valve membrane comprising:
   a disc made of a soft elastic material, said disc having a central axis, said disc having opposed first and second faces, said first face having a concave shape extending into said disc:
   a first slit extending into said disc from said first face;
   a second slit extending into said disc from said second face so that said second slit does not touch said first slit; and,
   wherein said disc has a needle hole connecting said first and second slits, said needle hole having a smaller diameter than the object to be placed through said needle hole.

2. The valve membrane of claim 1 wherein said second face is planar.

3. The valve membrane of claim 1 wherein said first slit is perpendicular to said first face.

4. The valve membrane of claim 1 wherein said second slit is perpendicular to said second face.

5. The valve membrane of claim 1 wherein said first slit passes through the center axis of said disc.

6. The valve membrane of claim 1 wherein said second slit passes through said center axis of said disc.

7. The valve membrane of claim 1 wherein said second face has a concave shape extending into said disc.

8. The valve membrane of claim 1 further comprising a third slit extending into said disc from said first face so that said third slit does not intersect said second slit and wherein said third slit intersects said first slit at said needle hole.

9. The valve membrane of claim 1 further comprising a third slit extending into said disc from said second face so that said third slit does not intersect said first slit and wherein said third slit intersects said second slit at said needle hole.

10. The valve membrane of claim 1 further comprising:
    a third slit extending into said disc from said first face so that said third slit does not intersect said second slit and wherein said third slit intersects said first slit at said needle hole; and,
    a fourth slit extending into said disc from said second face so that said fourth slit does not intersect said first or third slits, and wherein said fourth slit intersects said second slit at said needle hole.

11. The valve membrane of claim 10 wherein said first and third slits are aligned with said second and fourth slits.

12. The valve membrane of claim 1 further comprising a third slit extending into said disc from said first face so that said third slit does not intersect said second slit and wherein said third slit intersects said first slit at said needle hole.

13. The valve membrane of claim 12 wherein none of said slits are aligned.

14. A hemostasis valve membrane for use with a catheter introducer, having a cover and a frame, said valve membrane for inserting between the cover and frame of the catheter introducer body, said valve membrane comprising:
    a disc made of a soft elastic material, said disc having a central axis, said disc having opposed first and second faces;
    a first slit extending into said disc from said first face;
    a second slit extending into said disc from said second face so that said second slit does not touch said first slit;
    wherein said disc has a needle hole connecting said first and second slits, said needle hole having a smaller diameter than the object to be placed through said needle hole;
    a third slit extending into said disc from said first face so that said third slit does not intersect said second slit and wherein said third slit intersects said first slit at said needle hole; and,
    a fourth slit extending into said disc from said second face so that said fourth slit does not intersect said first or third slits, and wherein said fourth slit intersects said second slit at said needle hole.

15. The valve membrane of claim 14 wherein said first face has a concave shape extending into said disc.

16. The valve membrane of claim 14 wherein said first and third slits are aligned with said second and fourth slits.

17. A hemostasis valve membrane for use with a catheter introducer having a cover and a frame, said valve membrane for inserting between the cover and frame of the catheter introducer body, said valve membrane comprising:
    a disc made of a soft elastic material, said disc having a central axis, said disc having opposed first and second faces, said first face having a concave shape extending into said disc, said second face being planar;
    a first slit extending into said disc from said first face perpendicular to said first face, said first slit passing through said central axis of said disc;
    a second slit extending into said disc from said second face so that said second slit does not touch said first slit, said second slit being perpendicular to said second face, said second slit passing through said central axis of said disc;
    wherein said disc has a needle hole connecting said first and second slits along said central axis of said disc, said needle hole having a smaller diameter than the object to be placed through said needle hole;
    a third slit extending into said disc from said first face perpendicular to said first face so that said third slit does not intersect said second slit and wherein said third slit intersects said first slit at said needle hole; and,
    a fourth slit extending into said disc from said second face perpendicular to said second face so that said fourth slit does not intersect said first or third slits, and wherein said fourth slit intersects said second slit at said needle hole.

* * * * *